(12) United States Patent
Perkins et al.

(10) Patent No.: US 8,872,100 B1
(45) Date of Patent: Oct. 28, 2014

(54) ACTIVE CONTROL OF THERMAL EFFECTS ON OPTICAL COMPUTING DEVICES

(71) Applicant: Halliburton Energy Services, Inc., Houston, TX (US)

(72) Inventors: David L. Perkins, The Woodlands, TX (US); Li Gao, Katy, TX (US); Michael T. Pelletier, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 14/118,578

(22) PCT Filed: Jan. 15, 2013

(86) PCT No.: PCT/US2013/021564
§ 371 (c)(1),
(2), (4) Date: Nov. 19, 2013

(87) PCT Pub. No.: WO2014/112974
PCT Pub. Date: Jul. 24, 2014

(51) Int. Cl.
*G01N 21/17* (2006.01)
*G05D 23/19* (2006.01)
*G01N 21/59* (2006.01)
*G06E 3/00* (2006.01)

(52) U.S. Cl.
CPC ............... *G05D 23/19* (2013.01); *G01N 21/59* (2013.01); *G06E 3/001* (2013.01)
USPC ...................................... 250/238; 166/250.01

(58) Field of Classification Search
USPC ............... 250/238, 237 R, 216, 229; 166/66, 166/250.01, 250.14; 356/73, 432
See application file for complete search history.

(56) References Cited

U.S. PATENT DOCUMENTS

| | | | |
|---|---|---|---|
| 6,198,531 B1 | 3/2001 | Myrick et al. | |
| 6,529,276 B1 | 3/2003 | Myrick | |
| 6,832,025 B2 | 12/2004 | Fisher et al. | |
| 7,194,369 B2 | 3/2007 | Lundstedt et al. | |
| 7,268,884 B2 | 9/2007 | Kringlebotn et al. | |
| 7,830,519 B2 | 11/2010 | Mah et al. | |
| 7,920,258 B2 | 4/2011 | Myrick et al. | |
| 8,213,012 B2 | 7/2012 | Myrick et al. | |
| 8,823,939 * | 9/2014 | Freese et al. | 356/433 |
| 2009/0219512 A1 | 9/2009 | Myrick et al. | |
| 2011/0108719 A1 | 5/2011 | Ford et al. | |
| 2012/0150451 A1 | 6/2012 | Skinner et al. | |

OTHER PUBLICATIONS

International Search Report and Written Opinion for PCT/US2013/021564 dated Oct. 7, 2013.

* cited by examiner

*Primary Examiner* — Kevin Pyo
(74) *Attorney, Agent, or Firm* — McDermott Will & Emery LLP; Benjamin Fite

(57) ABSTRACT

Disclosed are systems and methods for actively controlling the temperature of an integrated computational element used in an optical computing device in order to affect its performance. One method includes providing an integrated computational element configured detect a characteristic of a substance and provide a transmission profile via a detector corresponding to the characteristic, and controlling a temperature of the integrated computational element in order to maintain the transmission profile within an optimal operating range.

21 Claims, 2 Drawing Sheets

ACTIVE CONTROL OF THERMAL EFFECTS ON OPTICAL COMPUTING DEVICES

This application is a National Stage entry of and claims priority to International Application No. PCT/US2013/021564, filed on Jan. 15, 2013.

BACKGROUND

The present invention relates to thermal management of optical computing devices and, more particularly, to actively controlling the temperature of an integrated computational element used in an optical computing device in order to affect its performance.

Optical computing devices, also commonly referred to as "opticoanalytical devices," can be used to analyze and detect one or more physical or chemical properties of a substance in real time. Such optical computing devices will often employ a processing element that optically interacts with the substance to determine quantitative and/or qualitative values of one or more physical or chemical properties of the substance. The processing element may be, for example, an integrated computational element (ICE), also known as a multivariate optical element (MOE). Electromagnetic radiation that optically interacts with the ICE is changed so as to be readable by a detector, such that an output of the detector can be correlated to the physical or chemical property of the substance being monitored.

An ICE typically includes a plurality of optical layers consisting of various materials whose index of refraction and size may vary between each layer. The layers may be strategically deposited and sized so as to selectively pass predetermined fractions of electromagnetic radiation at different wavelengths configured to substantially mimic a regression vector corresponding to a particular physical or chemical property of interest. As a result, the output light intensity from the ICE conveyed to the detector may be related to the physical or chemical property of interest for the substance.

It has been found, however, that temperature fluctuations can adversely impact the performance of an ICE, and potentially shift the resulting transmission spectrum or profile of the ICE. As a result, the output signals derived from the ICE may produce inaccurate measurements or concentrations of the physical or chemical property of interest for the substance. Therefore, it may prove advantageous to actively control the temperature of an ICE, and thereby maintain or control its operating performance in a predictable manner.

SUMMARY OF THE INVENTION

The present invention relates to thermal management of optical computing devices and, more particularly, to actively controlling the temperature of an integrated computational element used in an optical computing device in order to affect its performance.

In some embodiments, a method is disclosed and may include providing an integrated computational element with a transmission profile configured to detect a characteristic of a substance via a detector signal corresponding to the characteristic, and controlling a temperature of the integrated computational element in order to maintain the transmission profile within an optimal operating range.

In other embodiments, another method is disclosed and may include providing an integrated computational element with a transmission profile configured to detect a characteristic of a substance via a detector signal corresponding to the characteristic, and thermally controlling a temperature of the integrated computational element in order to spectrally shift the transmission profile such that it more accurately detects the characteristic of the substance.

In yet other embodiments, yet another method is disclosed and may include providing an integrated computational element with a first transmission profile configured to detect a first characteristic of a substance via a detector signal corresponding to the first characteristic, thermally controlling the integrated computational element in order to spectrally shift the first transmission profile to a second transmission profile, and detecting a second characteristic of the substance with the integrated computational element, the second characteristic of the substance corresponding to the second transmission profile.

The features and advantages of the present invention will be readily apparent to those skilled in the art upon a reading of the description of the preferred embodiments that follows.

BRIEF DESCRIPTION OF THE DRAWINGS

The following figures are included to illustrate certain aspects of the present invention, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

Figure 1:
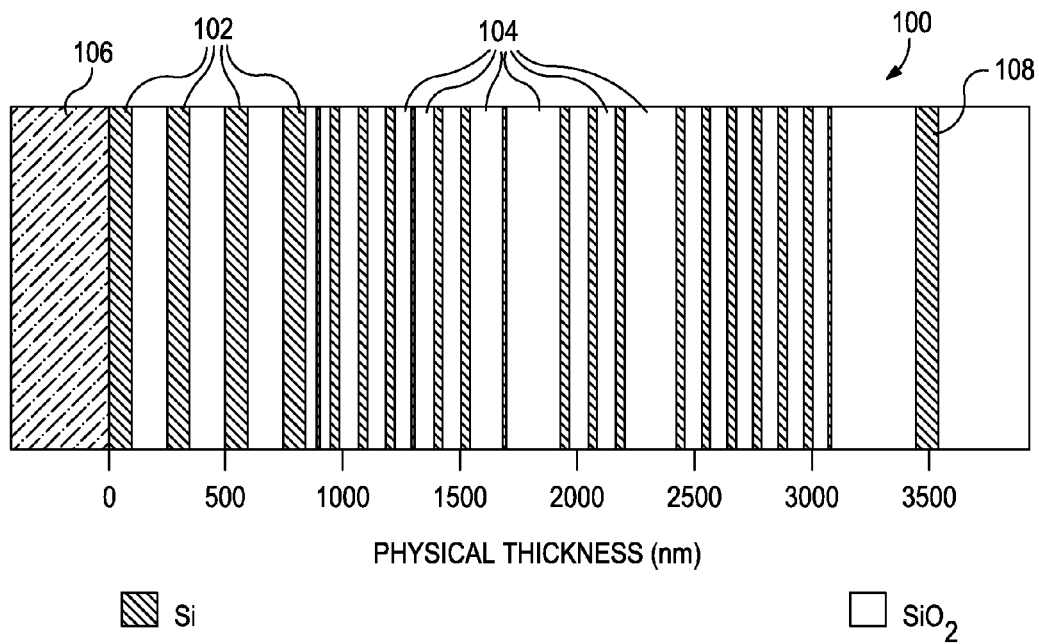
FIG. 1 illustrates an exemplary integrated computation element, according to one or more embodiments.

The present invention relates to thermal management of optical computing devices and, more particularly, to actively controlling the temperature of an integrated computational element used in an optical computing device in order to affect its performance.

Disclosed are exemplary systems and methods for controlling the temperature of an integrated computational element (ICE) as employed in an optical computing device. A significant and distinct advantage of ICE components is that they can be configured to specifically detect and/or measure a particular component or characteristic of interest of a substance, thereby allowing qualitative and/or quantitative analyses of the substance to occur without having to extract a sample and undertake time-consuming analyses of the sample at an off-site laboratory. Active temperature control of the ICE component may result in positively affecting the performance of the optical computing device, thereby providing better measurement predictability in known or variable temperature environments.

In some embodiments, the temperature of a given ICE may be actively controlled in order to regulate its resulting transmission profile. As a result, the optical computing device employing the ICE may be used in varying or extreme temperature environments while ensuring that the transmission profile will remain consistent over a broader temperature range. In other embodiments, the temperature of a given ICE may be actively controlled so as to finely tune the resulting transmission profile such that it more accurately mimics the regression vector of a particular chemical or physical characteristic of interest. In yet other embodiments, actively controlling the temperature of a given ICE may allow an operator to use a single ICE component to provide reasonable predictions of other closely-related characteristics, such as a chemical constituent that spectrally overlaps the transmission profile of the particular chemical or physical characteristic of interest.

As used herein, the term "characteristic" refers to a chemical, mechanical, or physical property of a substance. A characteristic of a substance may include a quantitative or qualitative value of one or more chemical constituents or compounds present therein or any physical property associated therewith. Such chemical constituents and compounds may be referred to herein as "analytes." Illustrative characteristics of a substance that can be monitored with the optical computing devices disclosed herein can include, for example, chemical composition (e.g., identity and concentration in total or of individual components), phase presence (e.g., gas, oil, water, etc.), impurity content, pH, alkalinity, viscosity, density, ionic strength, total dissolved solids, salt content (e.g., salinity), porosity, opacity, bacteria content, total hardness, combinations thereof, state of matter (solid, liquid, gas, emulsion, mixtures, etc.), and the like.

As used herein, the term "electromagnetic radiation" refers to radio waves, microwave radiation, infrared and near-infrared radiation, visible light, ultraviolet light, X-ray radiation and gamma ray radiation.

As used herein, the term "optical computing device" refers to an optical device that is configured to receive an input of electromagnetic radiation associated with a substance and produce an output of electromagnetic radiation from a processing element arranged within the optical computing device. The processing element may be, for example, an integrated computational element (ICE), also known as a multivariate optical element (MOE). The electromagnetic radiation that optically interacts with the processing element is changed so as to be readable by a detector, such that an output of the detector can be correlated to a particular characteristic of the substance. The output of electromagnetic radiation from the processing element can be reflected, transmitted, and/or dispersed electromagnetic radiation. Whether the detector analyzes reflected, transmitted, or dispersed electromagnetic radiation may be dictated by the structural parameters of the optical computing device as well as other considerations known to those skilled in the art. In addition, emission and/or scattering of the fluid, for example via fluorescence, luminescence, Raman, Mie, and/or Raleigh scattering, can also be monitored by optical computing devices.

As used herein, the term "optically interact" or variations thereof refers to the reflection, transmission, scattering, diffraction, or absorption of electromagnetic radiation either on, through, or from one or more processing elements (i.e., ICE or MOE components) or a substance being analyzed by the processing elements. Accordingly, optically interacted light refers to electromagnetic radiation that has been reflected, transmitted, scattered, diffracted, or absorbed by, emitted, or re-radiated, for example, using a processing element, but may also apply to interaction with a substance.

As mentioned above, the processing element used in the above-defined optical computing devices may be an integrated computational element (ICE). In operation, an ICE is capable of distinguishing electromagnetic radiation related to a characteristic of interest of a substance from electromagnetic radiation related to other components of the substance. Referring to FIG. 1, illustrated is an exemplary ICE 100, according to one or more embodiments. As illustrated, the ICE 100 may include a plurality of alternating layers 102 and 104, such as silicon (Si) and $SiO_2$ (quartz), respectively. In general, these layers 102, 104 consist of materials whose index of refraction is high and low, respectively. Other examples of materials might include niobia and niobium, germanium and germania, MgF, SiO, and other high and low index materials known in the art. The layers 102, 104 may be strategically deposited on an optical substrate 106. In some embodiments, the optical substrate 106 is BK-7 optical glass. In other embodiments, the optical substrate 106 may be another type of optical substrate, such as quartz, sapphire, silicon, germanium, zinc selenide, zinc sulfide, or various plastics such as polycarbonate, polymethylmethacrylate (PMMA), polyvinylchloride (PVC), diamond, ceramics, combinations thereof, and the like.

At the opposite end (e.g., opposite the optical substrate 106 in FIG. 1), the ICE 100 may include a layer 108 that is generally exposed to the environment of the device or installation. The number of layers 102, 104 and the thickness of each layer 102, 104 are determined from the spectral attributes acquired from a spectroscopic analysis of a characteristic of the substance being analyzed using a conventional spectroscopic instrument. The spectrum of interest of a given characteristic typically includes any number of different wavelengths. It should be understood that the exemplary ICE 100 in FIG. 1 does not in fact represent any particular characteristic of a given substance, but is provided for purposes of illustration only. Consequently, the number of layers 102, 104 and their relative thicknesses, as shown in FIG. 1, bear no correlation to any particular characteristic. Nor are the layers 102, 104 and their relative thicknesses necessarily drawn to scale, and therefore should not be considered limiting of the present disclosure. Moreover, those skilled in the art will readily recognize that the materials that make up each layer 102, 104 (i.e., Si and $SiO_2$) may vary, depending on the application, cost of materials, and/or applicability of the material to the given substance being analyzed.

In some embodiments, the material of each layer 102, 104 can be doped or two or more materials can be combined in a manner to achieve the desired optical characteristic. In addition to solids, the exemplary ICE 100 may also contain liquids and/or gases, optionally in combination with solids, in order to produce a desired optical characteristic. In the case of gases and liquids, the ICE 100 can contain a corresponding vessel (not shown), which houses the gases or liquids. Exemplary variations of the ICE 100 may also include holographic optical elements, gratings, piezoelectric, light pipe, digital light pipe (DLP), and/or acousto-optic elements, for example, that can create transmission, reflection, and/or absorptive properties of interest.

The multiple layers 102, 104 exhibit different refractive indices. By properly selecting the materials of the layers 102, 104 and their relative thickness and spacing, the ICE 100 may be configured to selectively pass/reflect/refract predetermined fractions of electromagnetic radiation at different wavelengths. Each wavelength is given a predetermined weighting or loading factor. The thickness and spacing of the layers 102, 104 may be determined using a variety of approximation methods from the spectrograph of the characteristic or analyte of interest. These methods may include inverse Fourier transform (IFT) of the optical transmission spectrum and structuring the ICE 100 as the physical representation of the IFT. The approximations convert the IFT into a structure based on known materials with constant refractive indices.

Further information regarding the structures and design of exemplary ICE elements is provided in *Applied Optics*, Vol. 35, pp. 5484-5492 (1996) and Vol. 29, pp. 2876-2893 (1990), which are hereby incorporated by reference.

The weightings that the layers 102, 104 of the ICE 100 apply at each wavelength are set to the regression weightings described with respect to a known equation, or data, or spectral signature. When electromagnetic radiation interacts with a substance, unique physical and chemical information about the substance may be encoded in the electromagnetic radiation that is reflected from, transmitted through, or radiated from the substance. This information is often referred to as the spectral "fingerprint" of the substance. The ICE 100 may be configured to perform the dot product of the electromagnetic radiation received by the ICE 100 and the wavelength dependent transmission function of the ICE 100. The wavelength dependent transmission function of the ICE is dependent on the layer material refractive index, the number of layers 102, 104 and the layer thicknesses. The ICE 100 transmission function is then analogous to a desired regression vector derived from the solution to a linear multivariate problem targeting a specific component of the sample. As a result, the output light intensity of the ICE 100 is related to the characteristic or analyte of interest.

The optical computing devices employing such an ICE may be capable of extracting the information of the spectral fingerprint of multiple characteristics or analytes within a substance and converting that information into a detectable output regarding the overall properties of the substance. That is, through suitable configurations of the optical computing devices, electromagnetic radiation associated with characteristics or analytes of interest in a substance can be separated from electromagnetic radiation associated with all other components of the substance in order to estimate the properties of the substance in real-time or near real-time. Further details regarding how the exemplary ICE 100 is able to distinguish and process electromagnetic radiation related to the characteristic or analyte of interest are described in U.S. Pat. Nos. 6,198,531; 6,529,276; and 7,920,258, incorporated herein by reference in their entirety.

Depending on the particular materials used to make the ICE 100, the index of refraction for each layer 102, 104 may spectrally shift in the presence of fluctuating temperatures, thereby having a detrimental effect on the overall performance of the ICE 100. One way to correct for temperature fluctuations, or otherwise reduce its adverse effects on the performance of the ICE 100, is to employ materials that exhibit a small or minimal dn/dT; i.e., change in refractive index over the change in temperature, where n=index of refraction and T=temperature. Using materials that exhibit a small dn/dT, however, may not always be feasible when trying to accurately mimic the regression vector of a particular characteristic of interest. Another way to correct for temperature fluctuations and its adverse effects on the ICE 100 would be to employ post-processing calculations that take into account the varying temperatures. Such processing, however, may add complexity and cost to the systems. As a result, other ways of accounting for spectral shift resulting from a temperature change are described below.

According to one or more embodiments of the disclosure, controlling the temperature of a given ICE can likewise control its resulting transmission profile and, therefore, impact its overall performance. For example, if the temperature of the ICE can be controlled to steady state, while the system temperature is allowed to change, the resulting transmission profile derived from the ICE will nonetheless remain constant. As a result, the performance of the ICE may remain consistent over a broader range of temperatures that the optical computing device is required to operate in.

Moreover, in embodiments where the system operates at steady state conditions, controlling the temperature of a given ICE may result in valuable shifts in the corresponding transmission profile such that the performance of the ICE may be finely tuned for the particular characteristic being analyzed. Tuning the performance of the ICE by altering its temperature may also result in accurate or reasonable predictions of other closely-related characteristics. For instance, an ICE configured to detect a particular chemical constituent may be thermally tuned such that the performance of the ICE is able to predict chemical constituents that have close spectral overlap.

To facilitate a better understanding of the present disclosure, the following examples of representative embodiments are given. In no way should the following examples be read to limit, or to define, the scope of the invention.

Figure 2:
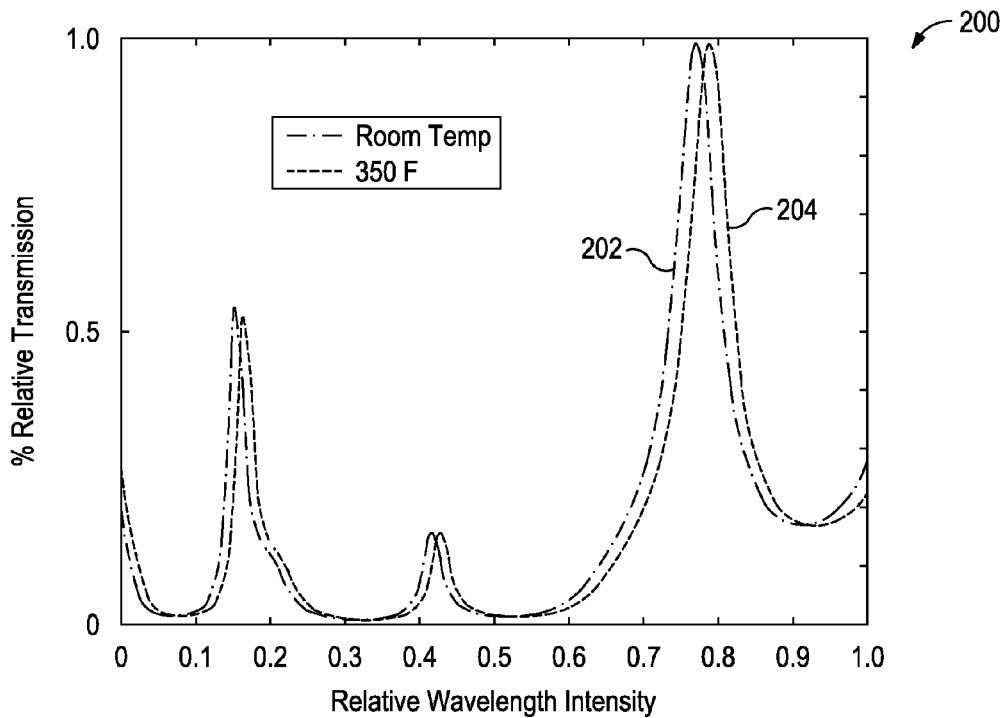
FIG. 2 illustrates a temperature dependence transmission profile for an exemplary integrated computational element, according to one or more embodiments.

Referring now to FIG. 2, with continued reference to FIG. 1, illustrated is a temperature dependence transmission profile 200 for an exemplary ICE, according to one or more embodiments. The ICE used to derive the illustrated transmission profile 200 may be similar to the ICE 100 of FIG. 1, and therefore will not be described again in detail. The ICE corresponding to the transmission profile 200 in FIG. 2, however, may be manufactured using thirteen layers (i.e., layers 102, 104 as discussed with reference to FIG. 1) of high and low refractive index materials, such as Si and $SiO_2$, respectively. Moreover, the ICE may be configured to detect methane in a fluid, such as the concentration of methane in a reservoir fluid found in the oil and gas industry.

The transmission profile 200 depicts the percent relative transmission (Y-axis) of the ICE in conjunction with the relative wavelength intensity (X-axis) of the same. More particularly, illustrated is a room temperature transmission profile 202 for the ICE and an elevated temperature transmission profile 204 for the same ICE. The room temperature transmission profile 202 depicts the spectral profile for the ICE while at room temperature (approximately 80° F.), and the elevated temperature transmission profile 204 depicts the spectral profile for the ICE after it is heated to about 350° F. (i.e., an expected downhole temperature). As can be seen, the transmission spectrum for the ICE shifts in response to the increased temperature. This shift in the transmission spectrum is wavelength dependent, meaning the effect is more pronounced at longer wavelengths and also results in subtle wavelength dependent intensity shifts.

The shift in the transmission spectrum of the ICE can at least partially be expected since Si is known to have a large temperature dependence on its refractive index (dn/dT). Accordingly, by allowing the ICE to undergo or experience this temperature shift, the prediction capabilities of the ICE for methane may be adversely affected, as indicated by the elevated temperature transmission profile 204. For instance, the standard error of calibration (SEC) for the ICE used in FIG. 2 at room temperature was calculated to be about 0.45 g/mL. When heated to 350° F., however, the SEC of the ICE saw an increase to about 9.60 g/mL (without any post-processing temperature correction). In other words, the temperature dependence transmission profile 200 demonstrates that the ability of the exemplary ICE to accurately predict methane will ultimately degrade or otherwise result in a greater degree of error upon experiencing an increase in temperature.

If the ICE is temperature controlled, however, such that the ICE is able to operate within an optimal or designed temperature range, the transmission profile may be maintained within an optimal operating range and the increase in SEC prediction error may therefore be minimized or eliminated altogether.

Accordingly, in at least one embodiment of the disclosure, the temperature of the ICE may be actively controlled or regulated so that the ICE is able to operate at an optimal temperature or otherwise within an optimal bandwidth. To accomplish this, the ICE may be thermally controlled using one or more thermal devices. In at least one embodiment, an optical computing device which employs or otherwise houses the ICE may include the thermal device(s) configured to regulate the temperature of the ICE such that an optimal operating temperature is maintained. The thermal device may include, but is not limited to, a thermoelectric cooler, a thermo-acoustic cooler, conductive heating devices or elements, radiative heater elements or devices (e.g., heat lamps), resistive heating devices or elements, heater coils, heat exchangers, fluid heaters (e.g., using water or another fluid, such as nitrogen, to manipulate the temperature), combinations thereof, and the like. In yet other embodiments, one or all of the conductive layers (e.g., the layers made of Si) may be used as resistive heaters. For instance, the resistance of the films at the optimum optical performance temperature could be used to regulate the process. As will be appreciated, this may prove advantageous in maintaining the heating function to the smallest possible mass.

The optimal operating temperature or temperature range for the given ICE may be room temperature, for example, but may equally be any other temperature or temperature range. The optimal operating temperature or temperature range may depend, at least in part, on the particular design of the ICE, such as the number and material of the layers and/or their relative thicknesses. In order to ensure that the ICE operates at its optimum level, the thermal device(s) may be configured to maintain the ICE at this optimal operating temperature or within the optimal temperature range. This may entail either heating or cooling the ICE, depending on which environment the optical computing device using the ICE is required to operate in. For instance, the ICE may have to be cooled using the thermal device if the optical computing device is used downhole where temperatures can reach upwards of 350° F. In other embodiments, the ICE may have to be heated using the thermal device if the optical computing device is used in frigid temperatures, such as on oil and gas pipelines in the Arctic, or deep sea pipelines at near freezing temperatures. By maintaining the ICE at its optimal temperature or within its optimal temperature range, the response of the ICE will continuously be optimized for detecting the analyte that it was initially designed for.

Those skilled in the art will readily appreciate that it is generally easier to thermostat a system above maximum operating temperature, and expect to heat the system. Doing so may ease operational difficulties encountered with refrigeration systems, including energy efficiency, complexity, condensation, and maintenance. In some embodiments, such an application may be supported in conjunction with a downhole transducer and adjacent heater, including pressure gauges, such as quartz pressure gauges, run at elevated temperatures in order to force a single temperature calibration requirement. Such embodiments are disclosed in co-owned U.S. Pat. No. 7,784,350, the contents of which are hereby incorporated by reference in their entirety.

Through proper testing of the particular ICE being used, the optimal operating temperature and/or temperature range may be determined. For instance, for a given ICE that is designed to operate at room temperature, a certain transmission profile 202 for that ICE will be conveyed while operating at room temperature. In some instances, the transmission profile 202 may be a reasonable predictor of a particular characteristic of interest of a substance, but due to miscellaneous manufacturing errors or operating conditions, may not perform optimally in predicting the characteristic of interest and instead may be improved upon. By altering the temperature of the ICE, such as by heating or cooling the ICE, the transmission profile 202 may be shifted or "tuned" such that it optimizes the regression vector for the characteristic of interest, thereby returning more accurate predictions. By doing so, the optimal temperature or temperature range at which to operate the particular ICE may be determined.

Those skilled in the art will readily appreciate the advantages this provides. For example, in many cases a batch of manufactured ICE components may result in several of the ICE components having slightly varying transmission profiles due to subtleties in their individual manufacturing. Controlling the temperature of a given ICE, as described herein, may be able to finely tune the shape of the resulting transmission profile, thereby correcting these small inconsistencies resulting from the manufacturing process. As a result, the performance of abnormal or slightly non-predictive ICE in a batch of ICE components may be normalized and otherwise obtain the most accurate measurements for the optical computing device.

Figure 3:
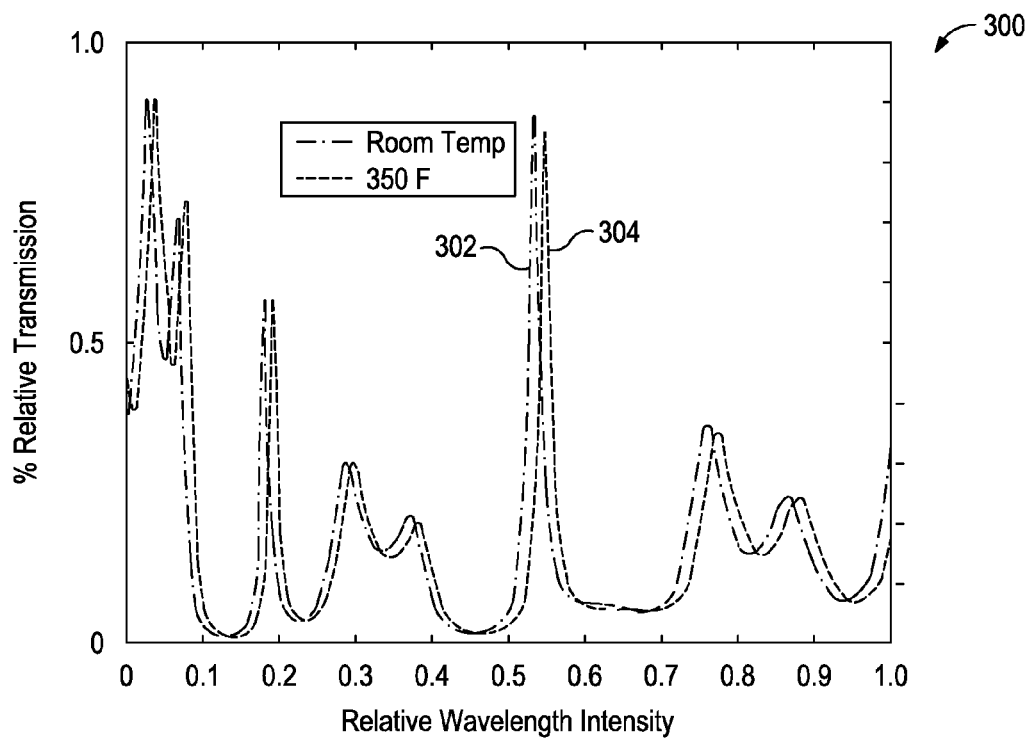
FIG. 3 illustrates a temperature dependence transmission profile for another exemplary integrated computational element, according to one or more embodiments.

Referring now to FIG. 3, with continued reference to FIGS. 1 and 2, illustrated is another temperature dependence transmission profile 300 for an exemplary ICE, according to one or more embodiments. Again, the ICE used to derive the transmission profile 300 may be similar to the ICE 100 of FIG. 1, and therefore will not be described again in detail. Similar to FIG. 2, the temperature dependence transmission profile 300 for the ICE provides the percent relative transmission (Y-axis) of the ICE in conjunction with its relative wavelength intensity (X-axis). In the example of FIG. 3, the ICE may be configured to detect a particular chemical constituent of a substance, such as propane ($C_3H_8$) as found in a fluid corresponding to the oil and gas industry.

FIG. 3 depicts a room temperature transmission profile 302 for the given ICE and a corresponding elevated temperature transmission profile 304 as recorded when the temperature of the ICE is increased to about 350° F. As depicted, the transmission spectrum for the ICE shifts in response to the increased temperature, thereby resulting in longer wavelengths. Moreover, there is also depicted a change in intensity in some of the peaks, and the spectrum may otherwise exhibit a slight tilt when the ICE is heated, such that the shifted peaks of the elevated temperature transmission profile 304 become less intense. As a result, the temperature dependence transmission profile 300 indicates that by allowing the ICE to undergo or experience this temperature shift, the prediction capabilities of the ICE for propane may be adversely affected.

While altering the temperature of the ICE may result in an inaccurate prediction of the characteristic for which the ICE was originally designed, such a temperature fluctuation may simultaneously result in the ICE being able to accurately or at least reasonably predict a closely-related analyte. For instance, while the ICE in FIG. 3 may be configured to detect propane, thermally controlling the ICE may shift the transmission profile 302 such that the ICE may then be able to accurately (or at least reasonably) detect ethane ($C_2H_6$), a chemical compound whose transmission profile spectrally overlaps that of propane. Therefore, according to one or more embodiments of the disclosure, a given ICE may be thermally controlled such that its transmission profile is shifted to a position where it is able to accurately predict an analyte that may overlap in a narrow spectral window, albeit an analyte that the ICE was not originally designed to detect.

In the illustrated example, where the ICE may be designed to detect propane (i.e., a "propane-predicting ICE"), the room temperature transmission profile 302 results in a standard error of calibration (SEC) of about 0.43 mol/L, which equates to about 3.5% relative error. When used to predict ethane at the same temperature (e.g., approximately 80° F.), however, the SEC was around 3.24 mol/L, which equates to about a 26.4% relative error. Accordingly, at the temperature at which the ICE was designed to operate, the ICE may reasonably predict propane with a relatively low SEC, but may be highly or at least unreasonably inaccurate when predicting ethane. According to the disclosure, however, thermally controlling the ICE may shift the transmission profile 302 such that an accurate prediction of ethane (or another closely-related carbon-based molecule) may be obtained.

Figure 4:
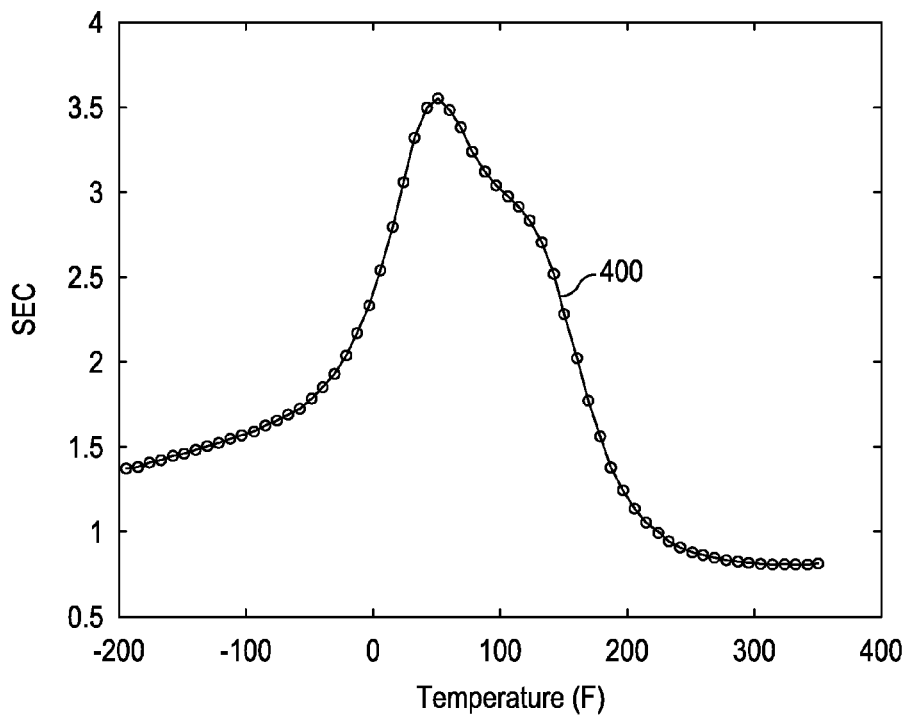
FIG. 4 illustrates an error plot that depicts the standard error of calibration for an integrated computational element as predicting a closely-related analyte across a temperature range, according to one or more embodiments.

Referring to FIG. 4, with continued reference to FIG. 3, illustrated is an error plot 400 depicting the standard error of calibration (SEC) for the ICE as predicting a closely-related analyte across a temperature range, according to one or more embodiments. Specifically, the error plot 400 depicts the SEC for ethane (Y-axis) by using the propane-predicting ICE of FIG. 3 as it is tested across a defined temperature range (X-axis). In other words, the propane-predicting ICE is thermally controlled over the indicated temperature range, and the SEC for ethane is calculated along such temperature range for each temperature shift.

The error plot 400 may be populated by calculating the dot product of the transmission profile of the propane-predicting ICE over a series of spectra which returns a number proportional to the concentration of ethane. Since the concentration of ethane is known through common spectroscopic techniques, a simple subtraction of the two values will return the error (i.e., the SEC). The SEC is essentially a sum of squares of the known value of ethane and the predicted value of ethane. Such a calculation or determination is made across the temperature range provided on the X-axis. For instance, the error plot 400 commences at approximately −200° F. where the spectrum for ethane is calculated and computationally combined with the theoretical prediction for ethane at that same temperature when using the propane-predicting ICE. The ICE is then incrementally heated and similar calculations are undertaken at each increment, thereby resulting in the depicted error plot 400.

As indicated by the error plot 400, the ICE is shown to be a poor predictor of ethane at room temperature (e.g., approximately 80° F.), where the error plot 400 indicates a SEC of approximately 3.5 mol/L. As the ICE is sequentially heated, or otherwise increased in temperature, the SEC for ethane is shown to correspondingly decrease. Upon heating the ICE to approximately 300° F., the SEC for ethane dips to around 0.5 mol/L where it becomes fairly predictable for ethane and may yield a reasonable ethane prediction of about 5.1% relative error, where relative error=(SEC/range)×100%, and where "range" is the difference between the maximum and minimum concentrations in the data.

Accordingly, the propane-predicting ICE may be employed to reasonably detect ethane if thermally controlled to a temperature of about 300° F. Those skilled in the art will readily recognize, however, that this does not mean that an ethane-predicting ICE could not be designed to more accurately predict ethane. Rather, the propane-predicting ICE at this particular temperature (i.e., approximately 300° F.) may be considered a reasonable substitute for predicting ethane if an error of around 5% was considered sufficient or reasonable. This may prove advantageous since many quality control errors (on both the high and the low sides) may be prevalent in manufacturing a particular ICE component, thereby yielding an "abnormal" or "unpredictive" ICE. By thermally controlling an abnormal or unpredictive ICE, an operator will be able to use such an ICE to predict a closely-related analyte within a reasonable error percentage. As a result, the time and cost of designing and manufacturing an ICE designed for a particular characteristic of interest may be advantageously saved.

In yet another embodiment of the disclosure, a given ICE may be thermally controlled in order to "tune" the ICE over a small spectral range, thereby allowing a single ICE component to detect multiple characteristics of a substance that may overlap in a narrow spectral window. For example, in reservoir fluids commonly found in the oil and gas industry, methane, ethane, and propane are three chemical constituents that overlap spectrally due to their similar chemical structures. In one or more embodiments, a single ICE may be used to detect each chemical constituent by thermally controlling the ICE across a given temperature range. At one temperature, for example, the ICE may be suitable for detecting methane, at a second temperature the ICE may be suitable for detecting ethane, and at a third temperature the ICE may be suitable for detecting propane. The ICE may be thermally controlled to the respective temperatures using one or more thermal devices, as generally discussed and described above.

Such embodiments may prove advantageous in that an operator may be able to employ a single ICE component to predict multiple characteristics or analytes. The ICE need only to be thermally controlled to the optimal temperature range for each characteristic, whereby an accurate prediction of the characteristic may be obtained. Such an application may save valuable space in optical computing devices, which are often compactly designed and configured to operate with a specific limited number of ICE components.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

The invention claimed is:

1. A method, comprising:
    providing an integrated computational element with a transmission profile configured to detect a characteristic of a substance via a detector signal corresponding to the characteristic; and
    controlling a temperature of the integrated computational element in order to maintain the transmission profile within an optimal operating range.

2. The method of claim 1, further comprising:
    arranging the integrated computational element in an optical computing device configured to optically interact with the substance;
    placing the optical computing device in an environment having an elevated temperature; and
    wherein, controlling the temperature of the integrated computational element comprises cooling the integrated computational element such that the temperature is maintained within the optimal temperature range.

3. The method of claim 1, further comprising:
    arranging the integrated computational element in an optical computing device configured to optically interact with the substance;
    placing the optical computing device in an environment having a reduced temperature; and
    wherein, controlling the temperature of the integrated computational element comprises heating the integrated computational element such that the temperature is maintained within the optimal temperature range.

4. The method of claim 1, wherein controlling the temperature of the integrated computational element further comprises thermally controlling the integrated computational element with one or more thermal devices.

5. The method of claim 4, further comprising cooling and/or heating the integrated computational element with the one or more thermal devices.

6. The method of claim 4, wherein the one or more thermal devices comprise at least one of a thermoelectric cooler, a thermo-acoustic cooler, a conductive heating device or element, a radiative heater, a resistive heating device or element, a heater coil, a heat exchanger, a fluid heater, combinations thereof, and the like.

7. The method of claim 1, further comprising detecting the characteristic of the substance with the integrated computational element.

8. The method of claim 1, wherein the integrated computational element comprises a plurality of layers made of high and low refractive index materials, respectively.

9. A method, comprising:
    thermally controlling a temperature of an integrated computational element having a transmission profile configured to detect a characteristic of a substance via a detector signal corresponding to the characteristic; and
    spectrally shifting the transmission profile such that it more accurately detects the characteristic of the substance.

10. The method of claim 9, wherein thermally controlling the temperature of the integrated computational element further comprises thermally controlling the integrated computational element with one or more thermal devices.

11. The method of claim 9, wherein thermally controlling the temperature of the integrated computational element comprises cooling and/or heating the integrated computational element with the one or more thermal devices.

12. The method of claim 9, wherein the one or more thermal devices comprise at least one of a thermoelectric cooler, a thermo-acoustic cooler, a conductive heating device or element, a radiative heater, a resistive heating device or element, a heater coil, a heat exchanger, a fluid heater, combinations thereof, and the like.

13. The method of claim 9, wherein thermally controlling the temperature of the integrated computational element is preceded by detecting the characteristic of the substance with the integrated computational element.

14. The method of claim 9, wherein thermally controlling the temperature of the integrated computational element is preceded by determining an optimal temperature or temperature range at which to operate the integrated computational element.

15. The method of claim 9, wherein the integrated computational element comprises a plurality of layers made of high and low refractive index materials, respectively.

16. A method, comprising:
    thermally controlling an integrated computational element having a first transmission profile configured to detect a first characteristic of a substance via a detector signal corresponding to the first characteristic;
    spectrally shifting the first transmission profile to a second transmission profile; and
    detecting a second characteristic of the substance with the integrated computational element, the second characteristic of the substance corresponding to the second transmission profile.

17. The method of claim 16, further comprising detecting the first characteristic of the substance with the integrated computational element.

18. The method of claim 16, wherein thermally controlling the integrated computational element further comprises cooling and/or heating the integrated computational element with one or more thermal devices.

19. The method of claim 18, wherein the one or more thermal devices comprise at least one of a thermoelectric cooler, a thermo-acoustic cooler, a conductive heating device or element, a resistive heating device or element, a heater coil, a heat exchanger, a fluid heater, combinations thereof, and the like.

20. The method of claim 18, further comprising:
    thermally controlling the integrated computational element in order to spectrally shift the first transmission profile to provide a third transmission profile; and
    detecting a third characteristic of the substance with the integrated computational element, the third characteristic of the substance corresponding to the third transmission profile.

21. The method of claim 18, further comprising:
    detecting the first characteristic when the integrated computational element is at a first temperature;
    detecting the second first characteristic when the integrated computational element is at a second temperature; and
    detecting the third characteristic when the integrated computational element is at a third temperature, wherein the first, second, and third temperatures are different.

* * * * *